United States Patent [19]

Gimson

[11] Patent Number: 4,887,023
[45] Date of Patent: Dec. 12, 1989

[54] CAPACITIVE SENSOR AND CIRCUIT FOR DETECTING CONTAMINATION OF GUARD ELECTRODE

[75] Inventor: Christopher J. Gimson, Bolton, United Kingdom

[73] Assignee: Mestra A.G., Reinach, Switzerland

[21] Appl. No.: 228,915

[22] PCT Filed: Jan. 30, 1987

[86] PCT No.: PCT/GB87/00064
§ 371 Date: Sep. 12, 1988
§ 102(e) Date: Sep. 12, 1988

[87] PCT Pub. No.: WO87/04792
PCT Pub. Date: Aug. 13, 1987

[30] Foreign Application Priority Data
Feb. 4, 1986 [GB] United Kingdom ............... 8602742

[51] Int. Cl.⁴ ..................... G01R 27/00; G01N 27/00
[52] U.S. Cl. ..................... 324/61 R; 324/61 P; 324/439; 324/448; 73/61.1 R; 73/61.2
[58] Field of Search ............... 324/61 R, 61 P, 60 C, 324/439, 446, 448, 450, 60 R, 60 CD; 73/61.1 R, 61.2, 304 C

[56] References Cited

U.S. PATENT DOCUMENTS

| | | | |
|---|---|---|---|
| 2,599,583 | 6/1952 | Robinson | 175/183 |
| 3,047,797 | 7/1962 | Borsboom | 324/448 X |
| 3,502,970 | 3/1970 | Thayer | 324/61 R |
| 3,694,742 | 9/1972 | Bergmanis | 324/61 QS |
| 3,808,523 | 4/1974 | Jobe | 324/446 |
| 3,860,882 | 1/1975 | Maltby | 330/26 |
| 4,451,894 | 5/1984 | Dougherty et al. | 73/304 C X |
| 4,459,541 | 7/1984 | Fielden et al. | 324/60 CD |
| 4,583,402 | 4/1986 | Myers et al. | 73/304 C |
| 4,626,774 | 12/1986 | Regtien | 324/61 R |

*Primary Examiner*—Reinhard J. Eisenzopf
*Assistant Examiner*—Jack B. Harvey
*Attorney, Agent, or Firm*—Spensley Horn Jubas & Lubitz

[57] ABSTRACT

An apparatus for detecting contamination of a capacitive sensor, comprising a guard electrode surrounding a portion of the sensor, and a circuit for supplying an excitation signal to the sensor and an identical excitation signal to the guard electrode. The circuit periodically isolates the guard electrode from the excitation signal, and detects the difference between the sensor output when the guard electrode is supplied with the excitation signal and when the guard electrode is isolated from the excitation, the detected difference being a function of the contamination of the guard electrode.

2 Claims, 3 Drawing Sheets

CAPACITIVE SENSOR AND CIRCUIT FOR DETECTING CONTAMINATION OF GUARD ELECTRODE

The present invention relates to an apparatus for detecting contamination of a capacitive sensor.

Capacitive sensors are used in many applications to identify materials placed between electrodes of the sensor. One example of the use of a capacitive sensor to determine the water content of oil is described in British Patent Specification No. 2,087,084. The circuit described in the above mentioned patent specification works extremely well but there is a tendency for the sensor to become contaminated with debris carried in the oil and water mixture the characteristics of which are to be determined and this can result in a considerable drift or instability in the sensor output.

In an attempt to overcome the problem of debris build up on a capacitive sensor it is known to shield exposed portions of the sensor with a guard electrode. The guard electrode is fed with an excitation signal which is identical in amplitude and phase to the signal supplied to the sensor and this has the effect of desensitizing those areas of the sensor which are surrounded by the guard. As debris builds up on the guard electrode there is no measurable effect on the output of the sensor until the build up of debris becomes so large as to neutralize the effect of the guard and introduce drift in the sensor output.

When dealing with fluid such as unrefined petroleum oil it is very difficult to estimate the amount of time taken for a particular level of contamination to build up on the guard electrode and therefore it is necessary to strip down the sensor structure to check for excessive contamination at regular intervals. On many occasions these inspections reveal no significant contamination but they must nevertheless be conducted to take account of worst case situations.

It is an object of the present invention to provide means for monitoring the build up of contamination on a capacitive sensor incorporating a guard electrode.

According to the present invention there is provided an apparatus for detecting contamination of a capacitive sensor, comprising a guard electrode surrounding a portion of the sensor, and a circuit for supplying an excitation signal to the sensor and an identical excitation signal to the guard electrode, wherein the circuit comprises means for periodically isolating the guard electrode from the excitation signal, and means for detecting the difference between the sensor output when the guard electrode is supplied with the excitation signal and when the guard electrode is isolated from the excitation signal, the detected difference being a function of the contamination of the guard electrode.

Preferably, the variation of the detected difference is monitored automatically and an output signal is generated as soon as a predetermined change in the detected difference occurs.

An embodiment of the present invention will now be described, by way of example, with reference to the accompanying drawings, in which.

Figure 1:
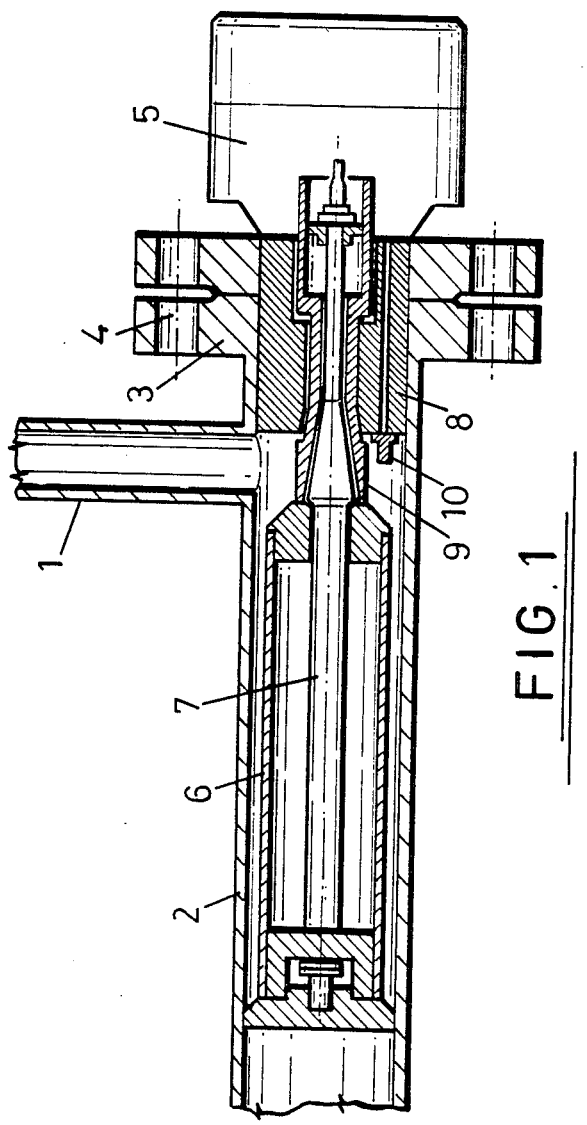
FIG. 1 is an illustration of a conventional capacitive sensor incorporating a guard electrode.

Referring to FIG. 1, the illustrated sensor is used to monitor the water content of oil supplied via an inlet 1 to a pressure vessel 2. The pressure vessel supports a flange 3 defining holes 4 to receive fixing bolts. A housing 5 is provided to receive circuitry which will be described below.

A cylindrical inner electrode 6 is supported on a rod 7 which extends through a boss 8 into the housing 5. A guard electrode 9 is arranged around the rod 7. Identical excitation signals are fed to the inner electrode 6 and the guard electrode 9 from the circuitry within the housing 5. The pressure vessel 2 is earthed and thus the structure defines a capacitor the plates of which are separated by an annular space that is filled with oil fed via inlet 1.

If the guard electrode 9 was not provided debris would rapidly accumulate around the rod 7 adjacent the boss 8 and the sensor output would be subject to drift. The earth electrode isolates the sensor output from the effects of debris build up until such time as a considerable volume of debris has accumulated. Thereafter the output of the sensor again begins to drift.

A temperature sensor 10 enables the circuitry 5 to compensate for changes in the oil temperature. There is however no means for determining whether or not changes in the sensor output result from changes in the water content of the oil fed to the pressure vessel or an excessive build up of debris on the guard electrode.

Figure 2:
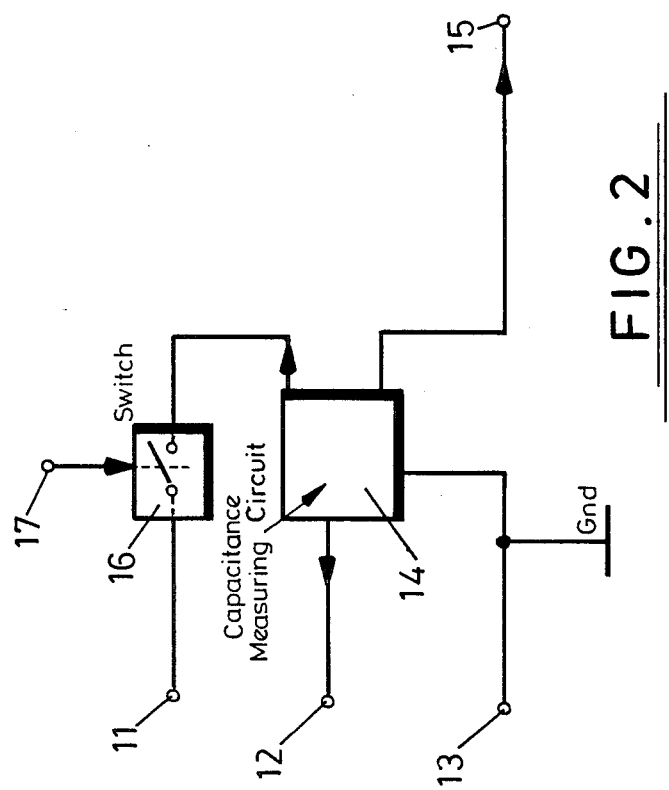
FIG. 2 is a schematic illustration of a circuit incorporated in the present invention for connection to the sensor of FIG. 1.

Referring now to FIG. 2, the illustrated circuit comprises terminals 11 and 12 which are connected respectively to the guard electrode 9 and the inner electrode 6. A ground electrode 13 is connected to the pressure vessel 2.

A capacitance measuring circuit 14 operating in accordance with British Patent Specification No. 2,087,084 is connected to the pressure vessel 2 and the inner electrode 6 and produces an output at terminal 15 which is a function of the capacitance of the sensor defined by the inner electrode and the pressure vessel. A switch 16 is normally closed so that the guard electrode 9 shields the sensor capacitor from the effects of debris build up. In accordance with the present invention however the switch 16 is periodically opened in response to a control input 17 so as to isolate the guard electrode 9. When the guard electrode 9 is isolated it no longer acts as a shield and the sensor output 15 accordingly changes by an amount which is a function of the amount of debris that has been built up on the guard electrode. By monitoring the change in the output 15 which occurs when the switch 16 is opened the build up of contamination on the guard electrode can effectively be monitored.

Figure 3:
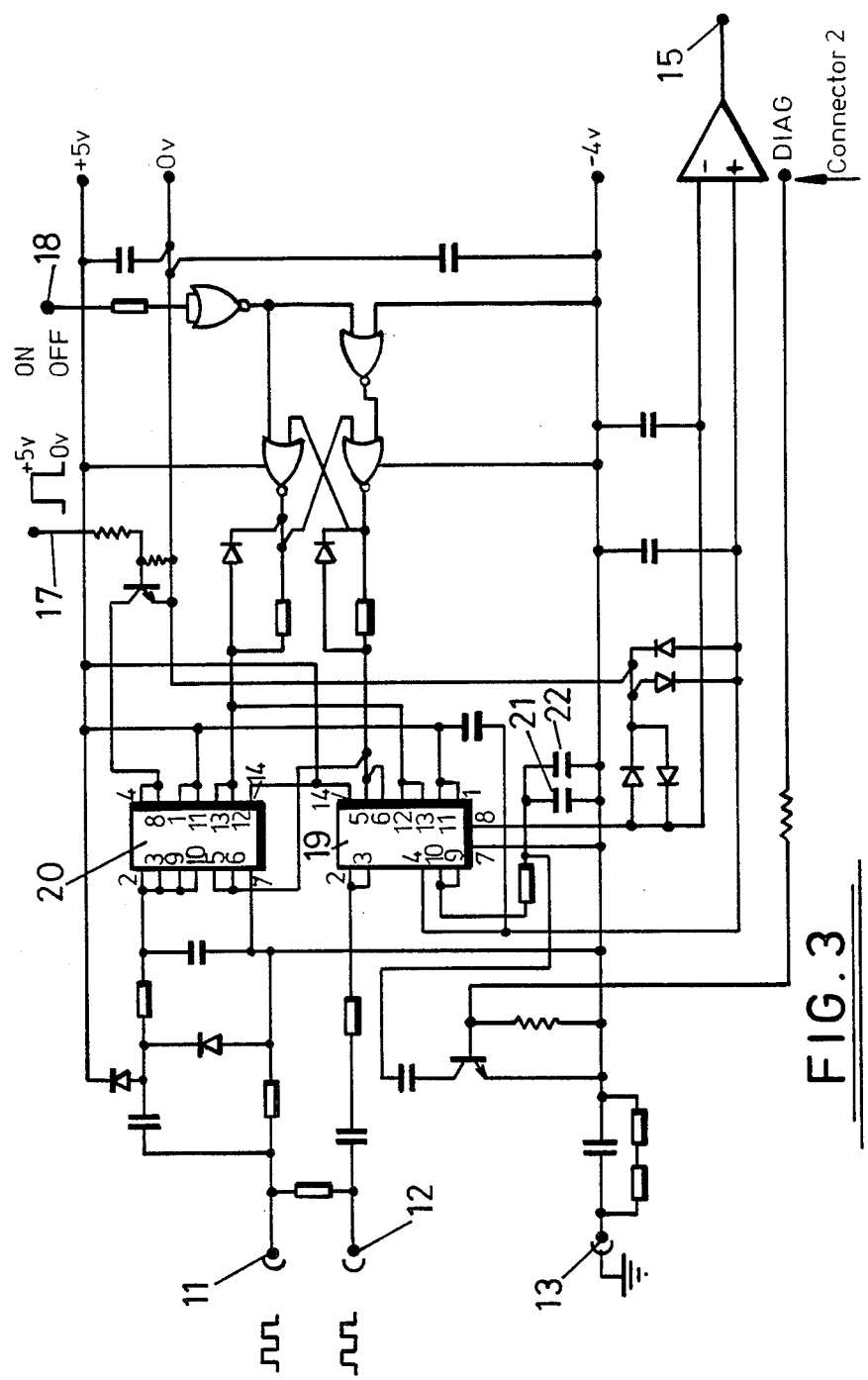
FIG. 3 is a detail circuit diagram of a circuit operating in accordance with British Patent Specification No. 2,087,084 but incorporating modifications in accordance with the present invention.

Referring now to FIG. 3 this shows in detail the circuit corresponding to the switch 16 and the capacitance measuring circuit 14 of FIG. 2. Square wave outputs of identical amplitude and phase appear at terminals 11 and 12, the frequency of the square wave being controlled by an input 18 to an astable multivibrator feeding integrated circuits (type 4066) 19 and 20. The circuit 20 generates the signal at output 11 and the circuit 19 generates the signal at output 12. A reference capacitance made up by capacitors 21 and 22 is used as a basis for determining the capacitance between the output 12 and ground terminal 13 in accordance with the techniques described in British Patent Specification No. 2,087,084.

The voltage at input 17 is normally five volts which causes the square wave signal to appear at output 11. Periodically the voltage at terminal 17 is reduced to zero volts which effectively turns off the guard by causing the terminal 11 to assume the ground potential. When this occurs the output 15 changes to a degree dependent not only upon the physical structure of the probe but also on the degree of contamination of the guard electrode 9. Thus a simple monitoring circuit can be connected to output 15 to automatically indicate when an undesirable level of contamination has built up. Alternatively the output 15 can simply drive for example a pen recorder so that a simple check of the resultant trace will enable the amount of contamination to be assessed for maintenance purposes.

I claim:
1. An apparatus for detecting contamination of a capacitive sensor, comprising a guard electrode surrounding a portion of the sensor, and a circuit for supplying an excitation signal to the sensor and an identical excitation signal to the guard electrode, wherein the circuit comprises means for periodically isolating the guard electrode from the excitation signal, and means for detecting the difference between the sensor output when the guard electrode is supplied with the excitation signal and when the guard electrode is isolated from the excitation signal, the detected difference being a function of the contamination of the guard electrode.

2. An apparatus according to claim 1, comprising means for generating an output signal in response to a predetermined change in the detected difference.

* * * * *